ns(12) United States Patent
Suzuki et al.

(10) Patent No.: US 10,082,462 B2
(45) Date of Patent: Sep. 25, 2018

(54) OPTICAL ELEMENT, TRANSMISSION PROBE, SAMPLE CONTAINER, OPTICAL DEVICE, AND IMMERSION TRANSMISSION MEASUREMENT METHOD

(71) Applicant: Yokogawa Electric Corporation, Musashino-shi, Tokyo (JP)

(72) Inventors: Yasuyuki Suzuki, Tokyo (JP); Yukihiro Nakamura, Tokyo (JP); Tetsushi Namatame, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 78 days.

(21) Appl. No.: 15/042,354

(22) Filed: Feb. 12, 2016

(65) Prior Publication Data
US 2016/0266039 A1 Sep. 15, 2016

(30) Foreign Application Priority Data

Mar. 13, 2015 (JP) ................. 2015-050473

(51) Int. Cl.
*G01N 21/00* (2006.01)
*G02B 17/00* (2006.01)
*G01N 21/59* (2006.01)
*G01N 21/85* (2006.01)
*G01N 21/03* (2006.01)

(52) U.S. Cl.
CPC ......... *G01N 21/59* (2013.01); *G01N 21/8507* (2013.01); *G02B 17/006* (2013.01); *G01N 2021/0307* (2013.01); *G01N 2201/0637* (2013.01); *G01N 2201/08* (2013.01); *G01N 2201/086* (2013.01)

(58) Field of Classification Search
None
See application file for complete search history.

(56) References Cited

U.S. PATENT DOCUMENTS

| | | | | |
|---|---|---|---|---|
| 3,733,130 A | | 5/1973 | Young | |
| 3,892,485 A | * | 7/1975 | Merritt | G01N 21/532 250/574 |
| 4,040,743 A | * | 8/1977 | Villaume | G01N 21/532 162/263 |
| 4,410,020 A | * | 10/1983 | Lorenz | B01L 3/021 141/284 |
| 4,829,186 A | * | 5/1989 | McLachlan | G01N 21/552 250/373 |
| 4,848,871 A | * | 7/1989 | Seidel | G01D 5/268 250/227.14 |

(Continued)

FOREIGN PATENT DOCUMENTS

| | | | | |
|---|---|---|---|---|
| EP | 0423367 A1 | | 4/1991 | |
| GB | 1189840 A | * | 4/1970 | ......... G01N 21/8507 |

(Continued)

*Primary Examiner* — Shawn Decenzo
*Assistant Examiner* — Jarreas C Underwood
(74) *Attorney, Agent, or Firm* — Sughrue Mion, PLLC (57) ABSTRACT

An optical element includes a main body formed of a light transmissive material and including an arc-shaped optical path, and a gap formed on the arc-shaped optical path in the main body. The gap may have a notch shape. The main body may have a semicircular plate shape. The main body may have a hemispherical shape.

16 Claims, 8 Drawing Sheets

(56) References Cited

U.S. PATENT DOCUMENTS

| | | | | |
|---|---|---|---|---|
| 4,893,935 | A | * | 1/1990 | Mandel ................ G01N 21/534 |
| | | | | 356/436 |
| 5,196,898 | A | * | 3/1993 | Tamura .............. G01N 21/8507 |
| | | | | 250/576 |
| 5,245,200 | A | * | 9/1993 | Fladda .................. G01N 15/06 |
| | | | | 250/227.25 |
| 5,266,486 | A | | 11/1993 | Fraatz et al. |
| 5,548,393 | A | | 8/1996 | Nozawa et al. |
| 5,742,157 | A | * | 4/1998 | Ishizuka ............ G01R 33/0322 |
| | | | | 324/244.1 |
| 5,946,084 | A | * | 8/1999 | Kubulins ............. G01N 21/431 |
| | | | | 356/128 |
| 6,037,770 | A | * | 3/2000 | Itoh .................... G01R 33/0322 |
| | | | | 324/244.1 |
| 6,466,323 | B1 | * | 10/2002 | Anderson ........... G01N 21/553 |
| | | | | 356/445 |
| 6,690,452 | B2 | * | 2/2004 | Wilks, Jr. ............. G01N 21/552 |
| | | | | 356/436 |
| 9,285,315 | B2 | * | 3/2016 | Gilan ................ G01N 21/0303 |

FOREIGN PATENT DOCUMENTS

| | | | | |
|---|---|---|---|---|
| GB | 1240991 | A | * 7/1971 | ......... G01N 21/8507 |
| GB | 2141537 | A | * 12/1984 | ......... G01N 21/8507 |
| JP | 07-072072 | A | 3/1995 | |
| JP | 2000-088749 | A | 3/2000 | |
| JP | 2009-250825 | A | 10/2009 | |
| JP | 2014238333 | A | 12/2014 | |
| JP | 2015-010934 | A | 1/2015 | |

* cited by examiner

OPTICAL ELEMENT, TRANSMISSION PROBE, SAMPLE CONTAINER, OPTICAL DEVICE, AND IMMERSION TRANSMISSION MEASUREMENT METHOD

CROSS-REFERENCE TO RELATED APPLICATION

This application claims priority from Japanese Patent Application No. 2015-050473 filed with the Japan Patent Office on Mar. 13, 2015, the entire content of which is hereby incorporated by reference.

BACKGROUND

1. Technical Field

The present disclosure relates to an optical element, a transmission probe, a sample container, an optical device, and an immersion transmission measurement method.

2. Description of the Related Art

Figure 11:
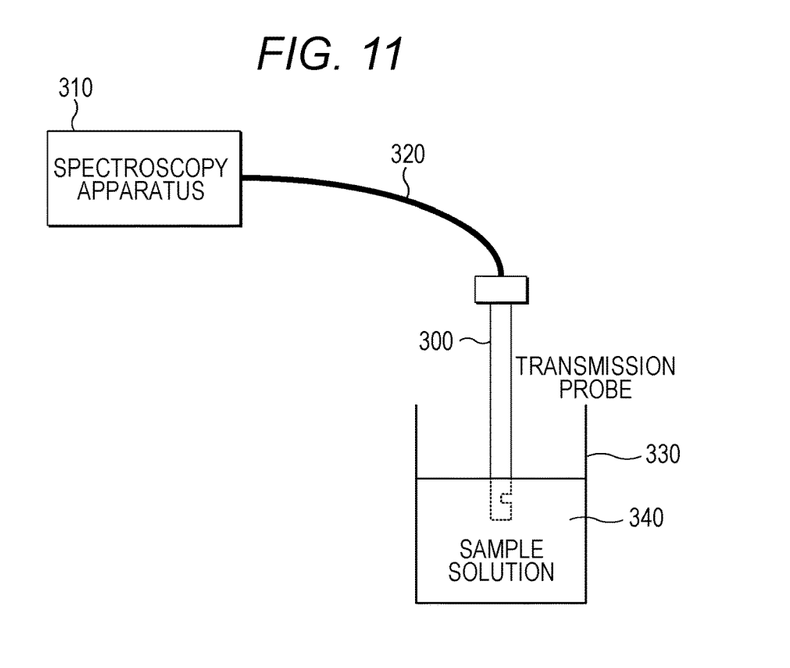
FIG. 11 illustrates the configuration of a spectral analysis system using a transmission probe.

A transmission probe is used when the light absorption characteristics, the transmission characteristics, and the like of a solution are measured. The transmission probe has a function of applying light from a light source to the solution, and a function of reflecting light having passed through the solution to return the light. In immersion transmission measurement using the transmission probe, for example, a transmission probe (immersion probe) 300 is connected to a spectroscopy apparatus 310 via an optical transmission path 320 such as an optical fiber as illustrated in FIG. 11. The transmission probe 300 is immersed directly in a sample solution 340 in a sample container 330.

In terms of the optical transmission path 320, one optical path may be used to propagate both irradiation light and measurement light that has passed through the sample solution 340. However, the optical paths for the irradiation light and the measurement light are normally separated. Moreover, there are pre-spectroscopy in which light dispersed in advance is applied, and post-spectroscopy in which white light is applied and the measurement light is dispersed.

Figure 12A:
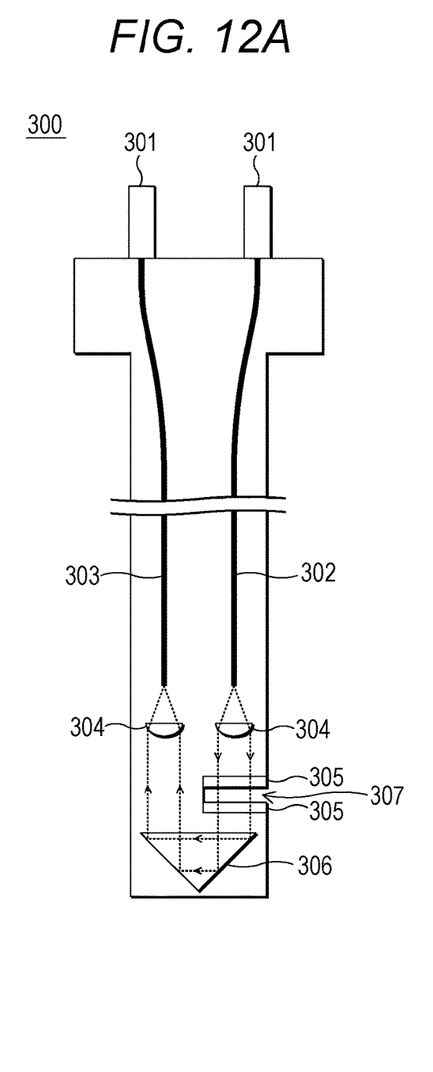
FIGS. 12A and 12B illustrate configuration examples of known transmission probes.
Figure 12B:
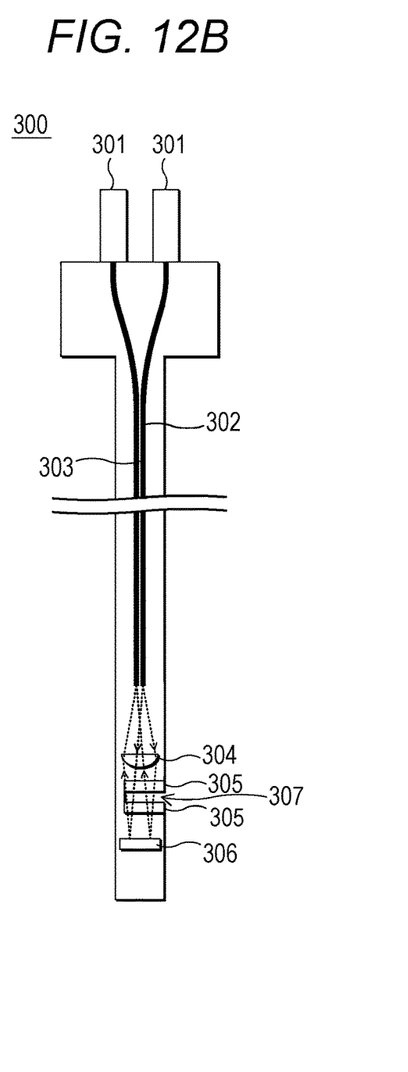

FIGS. 12A and 12B are diagrams illustrating configuration examples of known transmission probes. In the transmission probe of the type illustrated in FIG. 12A, the irradiation light passes through the sample solution once in one direction. In the transmission probe of the type illustrated in FIG. 12B, the irradiation light passes (reciprocates) through the sample solution twice. The transmission probe of the type illustrated in FIG. 12B is also called a transmission reflection probe (transflectance).

Both types of transmission probes have a rod-like shape to facilitate the immersion transmission measurements. A gap 307 that transmits light is formed on a side surface of each of the transmission probes. The sample solution enters the gap 307. These transmission probes include connectors 301 to be connected to the spectroscopy apparatus 310 via the optical transmission path 320, an irradiation purpose optical transmission path 302 that guides the irradiation light from the connector 301, a measurement purpose optical transmission path 303 that guides the measurement light to the connector 301, an optical system 304 such as a lens, windows 305 placed above and below the gap 307, and a reflector 306.

The prism reflector 306 is used in the type illustrated in FIG. 12A. A plane mirror as the reflector 306 is used in the type illustrated in FIG. 12B. In the type illustrated in FIG. 12B, light passes through the sample solution twice. Therefore, in a case of the same specification, the width (sample path) of the gap 307 in the transmission probe of the type illustrated in FIG. 12B is half the width of the gap 307 in the transmission probe of the type illustrated in FIG. 12A. Optical fibers and the like can be used as the irradiation purpose optical transmission path 302 and the measurement purpose optical transmission path 303.

A reference technique in this field is disclosed in, for example, JP-A-2009-250825.

SUMMARY

An optical element includes: a main body formed of a light transmissive material and including an arc-shaped optical path; and a gap formed on the arc-shaped optical path in the main body.

DESCRIPTION OF THE EMBODIMENTS

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The amount of light absorbed in a sample solution depends on the size of a sample path. Thus, an appropriate value is determined for the sample path in accordance with the light absorption characteristics and the like of the sample solution. For example, if the sample solution has a high absorbance for irradiation light, the sample path is reduced in size. Specifically, if light at a wavelength of approximately two μm is used to make a spectral analysis of water, a transmission probe having a sample path of approximately one mm is used in many cases.

Moreover, the diameter of the transmission probe is approximately 20 mm due to mechanical conditions such as heat resistance and pressure resistance. The depth of the gap 307 generally exceeds the radius of the transmission probe to secure a light transmission area in the sample solution.

If the gap 307 is deepened in the case where the sample path of the gap 307 is short, the sample solution does not easily enter the gap 307. If the sample solution does not easily enter the gap 307, the gap 307 may not be filled with the sample solution upon measurements. In this case, the measurement accuracy may be reduced. Moreover, in the case where, for example, the sample solution under reaction conditions is measured, if the sample solution is trapped in the gap 307 and the sample solution in the gap 307 is not replaced, it becomes difficult to obtain the latest state (a measurement value) of the sample solution.

An object of the present disclosure is to facilitate the entry of the sample solution into the gap when light is applied to the sample solution in the gap to take transmission measurements.

An optical element according to an aspect of the present disclosure (the present optical element) includes: a main body formed of a light transmissive material and including an arc-shaped optical path; and a gap formed on the arc-shaped optical path in the main body.

In the present optical element, the gap may have a notch shape.

In the present optical element, the main body may have a semicircular plate shape.

The present optical element may further include a flange portion provided to a diameter portion of the main body having the semicircular plate shape.

In the present optical element, the main body may have a hemispherical shape.

The present optical element may further include an inclined surface or curved surface formed at one corner on a notched side of the gap.

A transmission probe according to an aspect of the present disclosure includes: the present optical element; an irradiation purpose optical transmission path configured to emit irradiation light to the optical element such that total reflection occurs on an inner surface of the optical path of the optical element; and a measurement purpose optical transmission path configured to receive, as measurement light, return light passing through the gap of the optical element to be emitted from the optical path.

A sample container according to an aspect of the present disclosure includes: the present optical element; and an inner surface to which the optical element is attached.

An optical device according to an aspect of the present disclosure, which is to be attached to the sample container, includes: an irradiation purpose optical transmission path configured to emit irradiation light to the optical element such that total reflection occurs on an inner surface of the optical path of the optical element; and a measurement purpose optical transmission path configured to receive, as measurement light, return light passing through the gap of the optical element to be emitted from the optical path.

An immersion transmission measurement method according to an aspect of the present disclosure includes: attaching the optical element according to claim 1 to an inner surface of a sample container; emitting irradiation light from outside the sample container to the optical element such that total reflection occurs on an inner surface of the optical path of the optical element; and receiving, as measurement light, return light passing through the gap of the optical element to be emitted from the optical path.

The optical element is used for, for example, immersion transmission measurements. According to the optical element, it is possible to facilitate the entry of a sample solution into the gap when light is applied to the sample solution in the gap to take transmission measurements.

Figure 1:
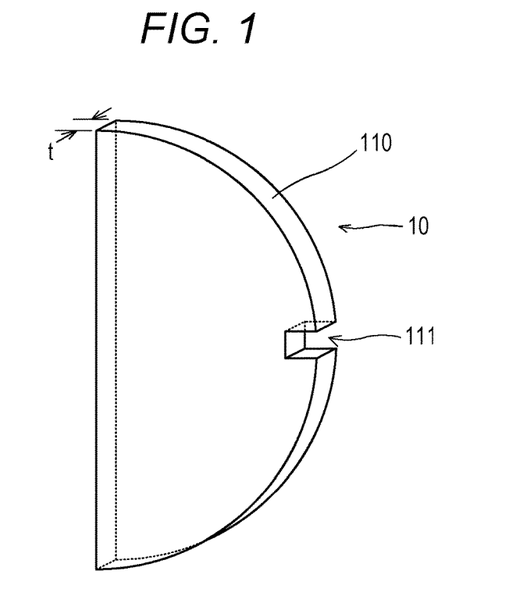
FIG. 1 illustrates a transmission probe specific optical element according to a first example of the embodiment.

An embodiment of the present disclosure will be hereinafter described with reference to the drawings. FIG. 1 illustrates a transmission probe specific optical element 10 according to a first example of the embodiment. As illustrated in the figure, the transmission probe specific optical element 10 includes a main body 110. The main body 110 is formed to have a semicircular plate shape with a thickness t. The transmission probe specific optical element 10 includes a notch-shaped gap 111 for allowing the entry of the sample solution on part of a semi-circumference of the main body 110.

Both walls of the gap 111 are formed in such a manner as to be substantially perpendicular to a tangent line to the semi-circumference at a middle position of the gap 111. The bottom of the gap 111 may have any shape. In this example, the gap 111 is formed at the midpoint on the semi-circumference. The gap 111 may be formed at another location on the semi-circumference instead.

The main body 110 of the transmission probe specific optical element 10 is made of a material that transmits light used for measurements. For example, quartz glass, diamond, or sapphire can be used as the material. A fluorine based plastic, such as PCTFE (poly-chloro-tri-fluoro-ethylene) that is a non-crystalline resin, may be used as the material. This is suitable in the case where near infrared light is used as the light used for measurements. Any other material can be used.

Figure 2:
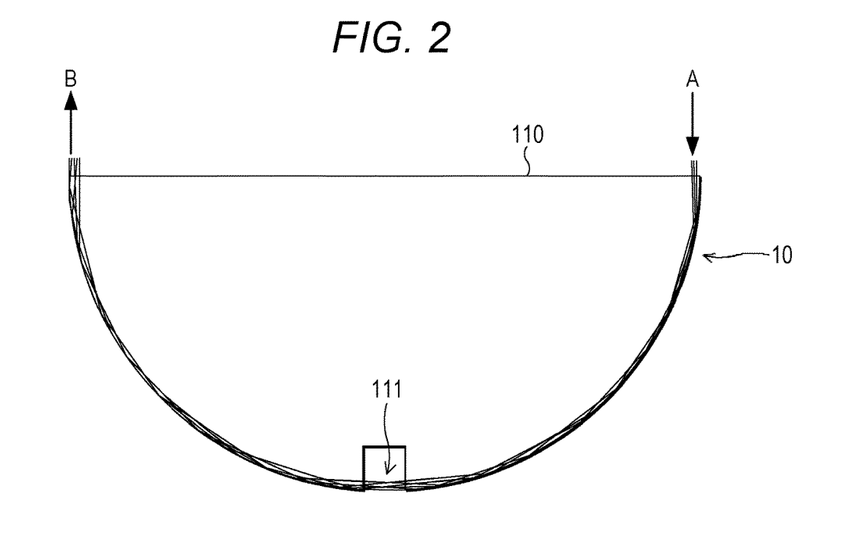
FIG. 2 illustrates the propagation of light along a semi-circumference in the transmission probe specific optical element.

When light is incident on an end A of a diameter portion of the semicircle of the main body 110 of such a transmission probe specific optical element 10 from a direction substantially perpendicular to the diameter portion as illustrated in FIG. 2, the light travels along an arc (an arc-shaped optical path) of the circumference while repeating total reflection inside the semi-circumference. The light further travels along the circumference across the gap 111 and goes out from an end B on the opposite side. In other words, the main body 110 of the transmission probe specific optical element 10 includes an arc-shaped optical path. The gap 111 is formed on the arc-shaped optical path in the main body 110.

When the main body 110 of the transmission probe specific optical element 10 is made of quartz glass and water is used as an external substance corresponding to the sample solution, if an angle of incidence of light (an angle with respect to a direction perpendicular to the diameter portion of the semicircle of the main body 110 of the transmission probe specific optical element 10) is approximately 10 degrees at the maximum, the light can be propagated to the end B. This has been confirmed using an equation expressing the critical angle in terms of calculation.

Figure 3A:
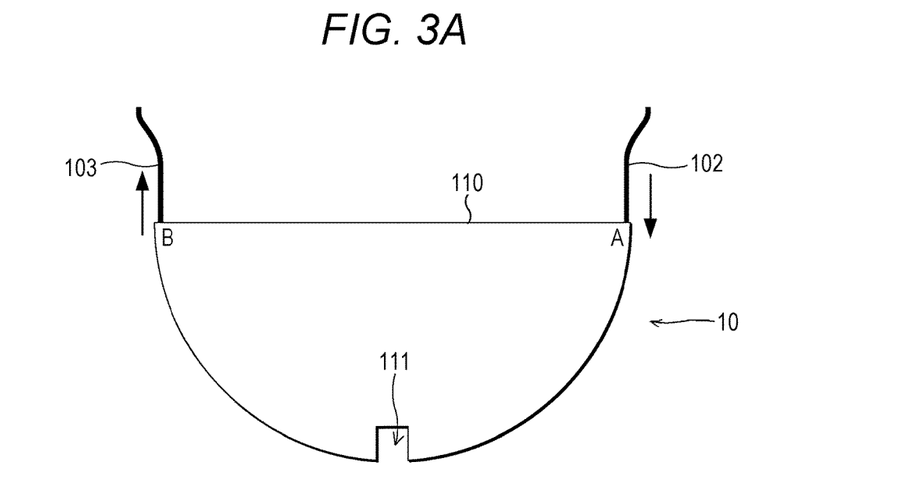
FIGS. 3A and 3B illustrate the entrance of illumination light and the emission of measurement light in the transmission probe specific optical element.

Thus, as illustrated in FIG. 3A, for example, by placing an emitting end of an irradiation purpose optical transmission path 102 such that light is incident on the end A substantially perpendicularly to the diameter portion of the semicircle and placing an incident end of a measurement purpose optical transmission path 103 at the end B, it is possible to allow irradiation light from the irradiation purpose optical transmission path 102 to pass through the gap 111 and to guide the light (measurement light) that has passed through the gap 111 to the measurement purpose optical transmission path 103.

The light travels along an inner side of the circumference in the main body 110 of the transmission probe specific optical element 10. Hence, even if the gap 111 is formed extremely shallowly, the light can pass through the gap 111. Accordingly, the entry of the sample solution into the gap 111 can be facilitated with a simple configuration by applying the transmission probe specific optical element 10 to a head section of a transmission probe.

It is preferable that light be incident on a position as close to the circumference as possible in the end A. Moreover, it is effective that the thickness t (see FIG. 1) of the main body 110 of the transmission probe specific optical element 10 is approximately the diameter of the incident light. Hence, the thickness t of the main body 110 of the transmission probe specific optical element 10 may be substantially equal to the diameter of an optical fiber used as the irradiation purpose optical transmission path 102.

Figure 3B:
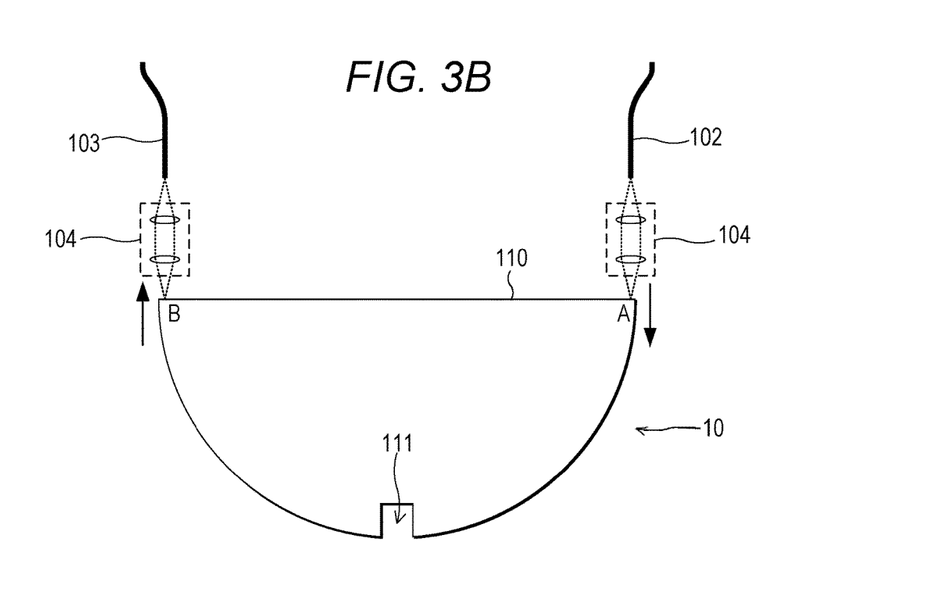

Alternatively, as illustrated in FIG. 3B, the irradiation light from the irradiation purpose optical transmission path 102 may be incident on the end A of the main body 110 via an optical system 104 including a lens and the like. Furthermore, the light (measurement light) that has passed through the gap 111 may be guided from the end B of the main body 110 to the measurement purpose optical transmission path 103 via the optical system 104. The optical system 104 on the irradiation purpose optical transmission path 102 side may be configured to condense the irradiation light to guide it to the end A. If the irradiation light from the irradiation purpose optical transmission path 102 is light with high straightness as in laser light, the optical system 104 may guide the irradiation light as parallel light to the end A.

The arc surface and both side surfaces of the semi-circumference, excluding the gap 111 portion (including both walls of the gap 111), of the main body 110 of the transmission probe specific optical element 10 may be coated to reflect the light used for measurements. For example, silver, gold, copper, zinc, aluminum, and potassium can be used as a coating agent.

Figure 4:
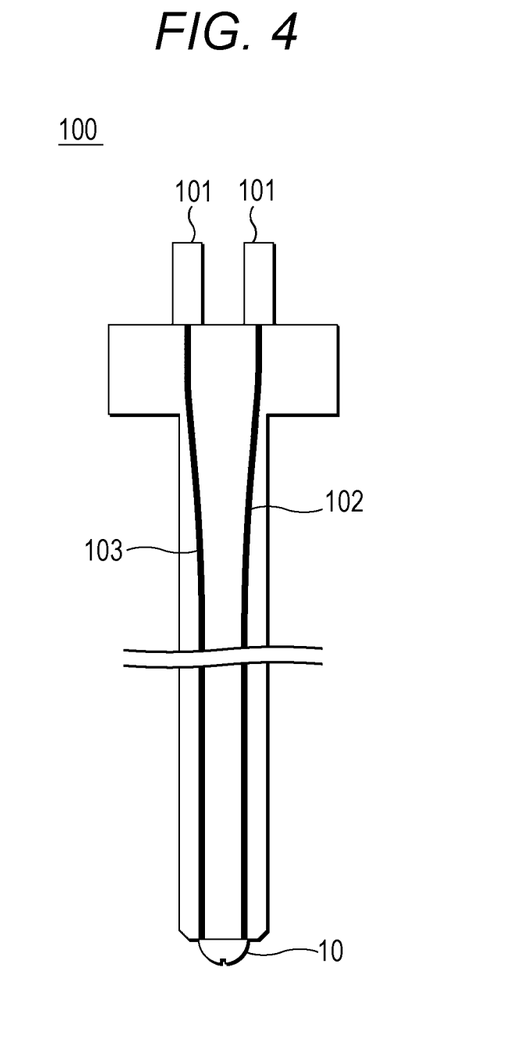
FIG. 4 illustrates a transmission probe including the transmission probe specific optical element.

Such a transmission probe specific optical element 10 can be used as a component of a transmission probe 100 as illustrated in FIG. 4. The transmission probe 100 is provided with: the transmission probe specific optical element 10; and connectors 101, the irradiation purpose optical transmission path 102 and the measurement purpose optical transmission path 103 which are included in a main body of the transmission probe 100. The connectors 101 are connected to a spectroscopy apparatus via the optical transmission paths.

The irradiation purpose optical transmission path 102 guides the irradiation light from the connector 101. In other words, the irradiation purpose optical transmission path 102 emits the irradiation light to the transmission probe specific optical element 10 such that total reflection occurs on an inner surface of the arc-shaped optical path of the transmission probe specific optical element 10. In other words, the irradiation purpose optical transmission path 102 allows the irradiation light to enter the end A of the main body 110 substantially perpendicularly to the diameter portion of the semicircle.

The measurement purpose optical transmission path 103 guides the measurement light to the connector 101. In other words, the measurement purpose optical transmission path 103 receives, as the measurement light, return light that passes through the gap 111 of the transmission probe specific optical element 10 and is emitted from the arc-shaped optical path of the transmission probe specific optical element 10.

The transmission probe specific optical element 10 is attached to a distal end of the main body of the transmission probe 100. A spectral analysis can be made by immersing the transmission probe specific optical element 10 in the sample solution. Consequently, it is possible to provide the transmission probe 100 that allows the sample solution to enter the gap easily.

In the transmission probe 100 illustrated in FIG. 4, the optical system 104 including a lens and the like may be interposed between the main body 110 of the transmission probe specific optical element 10 and the irradiation purpose optical transmission path 102, and/or between the main body 110 of the transmission probe specific optical element 10 and the measurement purpose optical transmission path 103, as described above.

Figure 5A:
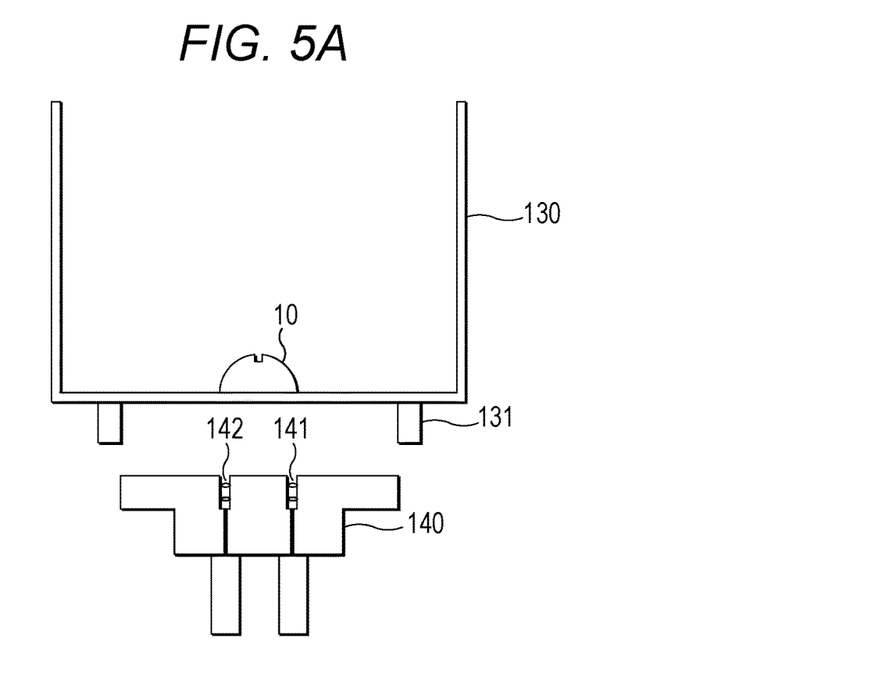
FIGS. 5A and 5B illustrate a sample container to which the transmission probe specific optical element is attached.

Alternatively, as illustrated in FIG. 5A, the transmission probe specific optical element 10 may be attached to an inside (an inner surface, for example, a bottom surface) of a sample container 130. In this case, an optical device 140 including an irradiation purpose optical transmission path 141 and a measurement purpose optical transmission path 142 is placed outside the sample container 130 to enable a spectral analysis of the sample solution in the sample container 130. The attachment position (the inner surface of the sample container 130 where the transmission probe specific optical element 10 is attached) of the transmission probe specific optical element 10 may be the bottom surface or side surface of the sample container 130.

In this case, a guide member 131 serving as a positioning member of the optical device 140 may be formed on the sample container 130. The guide member 131 is provided to enable the entrance of the irradiation light from the irradiation purpose optical transmission path 141 into an appropriate position of the main body 110 of the transmission probe specific optical element 10, and the entrance of the measurement light emitted from the main body 110 of the transmission probe specific optical element 10 into the measurement purpose optical transmission path 142.

Figure 5B:
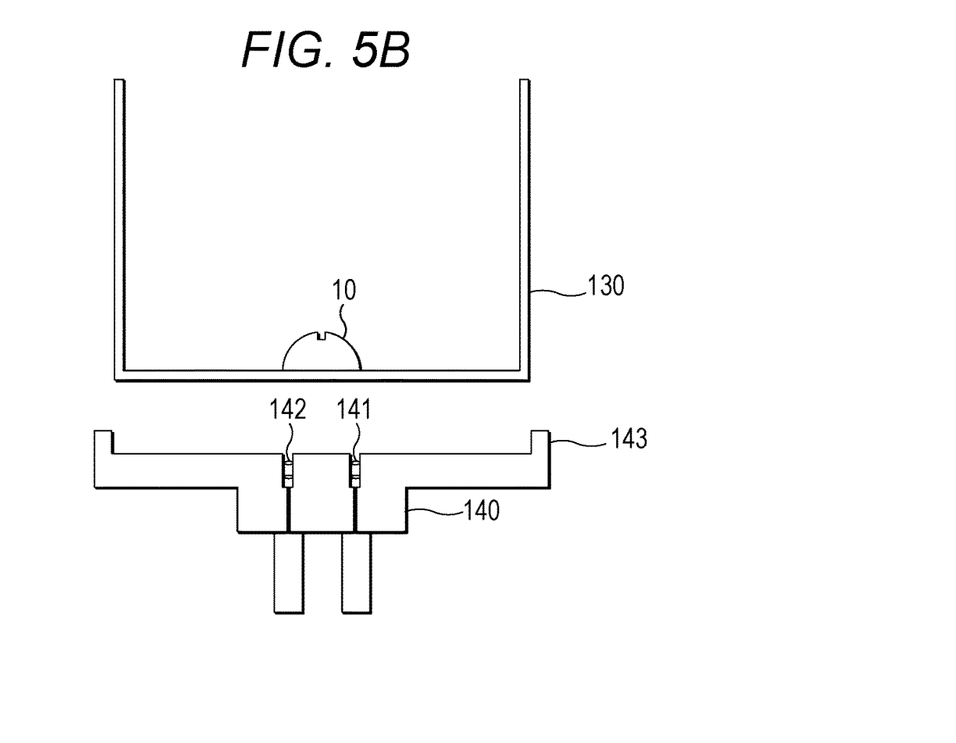

As illustrated in FIG. 5B, a positioning purpose guide member 143 having a similar function to that of the guide member 131 may be provided to the optical device 140.

The sample container 130 to which the transmission probe specific optical element 10 is attached is circulated in, for example, a sterilized state. The sample container 130 is suitable for a biochemical use for one use only, and a hazardous chemical substance measurement use.

An immersion transmission measurement method using such a sample container 130 can also be expressed as follows: the method includes attaching the transmission probe specific optical element 10 to the inner surface of the sample container 130, emitting the irradiation light to the transmission probe specific optical element 10 from outside the sample container 130 such that total reflection occurs on the inner surface of the optical path of the transmission probe specific optical element 10, and receiving, as the measurement light, the return light that passes through the gap 111 of the transmission probe specific optical element 10 and is emitted from the optical path.

Figure 6:
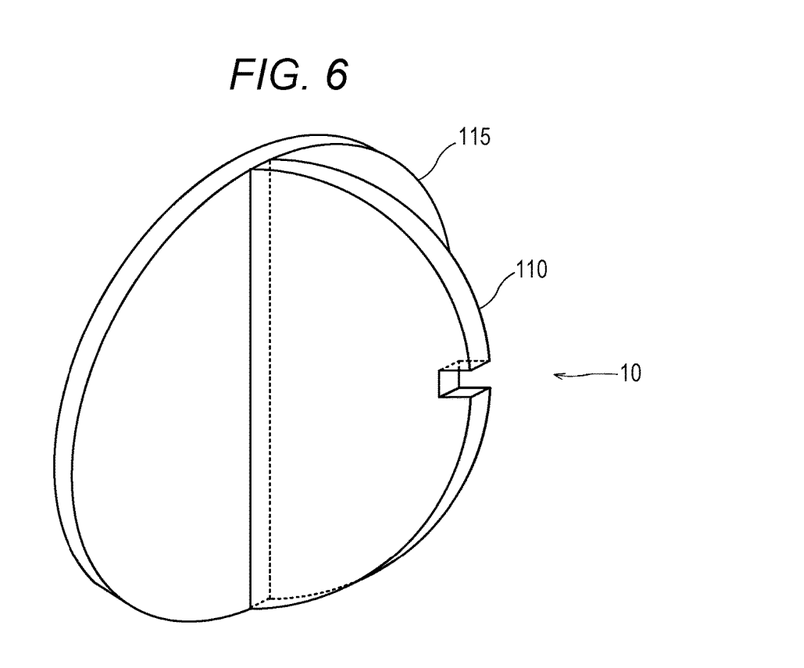
FIG. 6 illustrates a transmission probe specific optical element including a flange portion.

Moreover, as illustrated in FIG. 6, in order to facilitate the handling of the transmission probe specific optical element 10, a flange portion 115 may be formed on the diameter portion of the main body 110 of the transmission probe specific optical element 10. In other words, the transmission probe specific optical element 10 may further include the flange portion 115 provided to the diameter portion of the semicircular plate-shaped main body 110. A user can use the flange portion 115 to, for example, hold or fix the transmission probe specific optical element 10. The flange portion 115 may be formed as part of the optical path or formed outside the optical path (to avoid the optical path).

Figure 7:
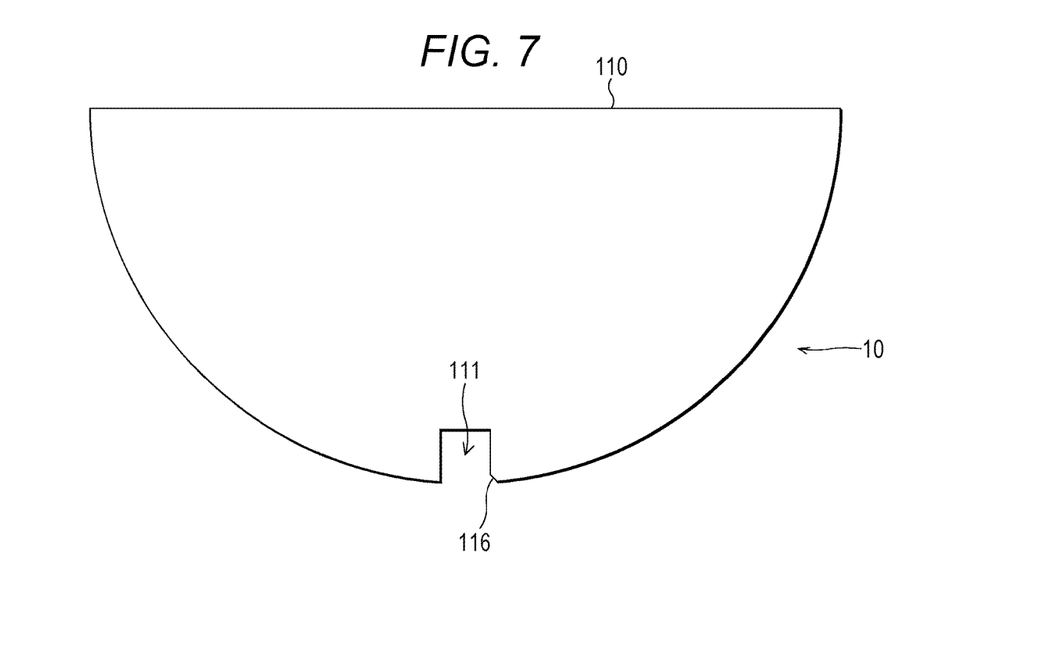
FIG. 7 illustrates a transmission probe specific optical element including an inclined surface formed at a gap.

As illustrated in FIG. 7, an inclined surface or curved surface (rounding) may be formed at one corner 116 on the notched side of the gap 111. In other words, the transmission probe specific optical element 10 may further include an inclined or curved surface formed at one corner on the notched side of the gap 111. Consequently, it is possible to reduce the amount of scattering in an outer circumferential direction of the irradiation light emitted from the gap 111. As a result, the amount of the measurement light can be increased.

Figure 8:
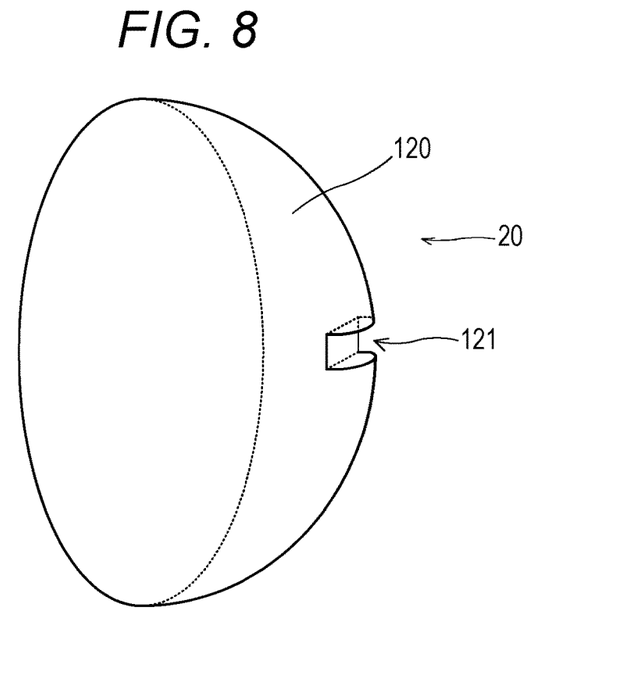
FIG. 8 illustrates a transmission probe specific optical element according to a second example of the embodiment.

Next, a second example of the embodiment will be described. FIG. 8 illustrates a transmission probe specific optical element 20 according to the second example of the embodiment. As illustrated in the figure, the transmission probe specific optical element 20 includes a main body 120. The main body 120 is formed to have a hemispherical shape. A notch-shaped gap 121 for allowing a sample solution to enter is formed on part of a hemispherical surface of the main body 120 of the transmission probe specific optical element 20.

Both walls of the gap 121 are formed in such a manner as to be substantially perpendicular to a tangent plane to the hemispherical surface at the middle position of the gap 121. The bottom of the gap 121 may have any shape. In the example, the gap 121 is formed at the top of the hemisphere. The gap 121 may be formed at another location on the hemispherical surface instead.

Figure 9:
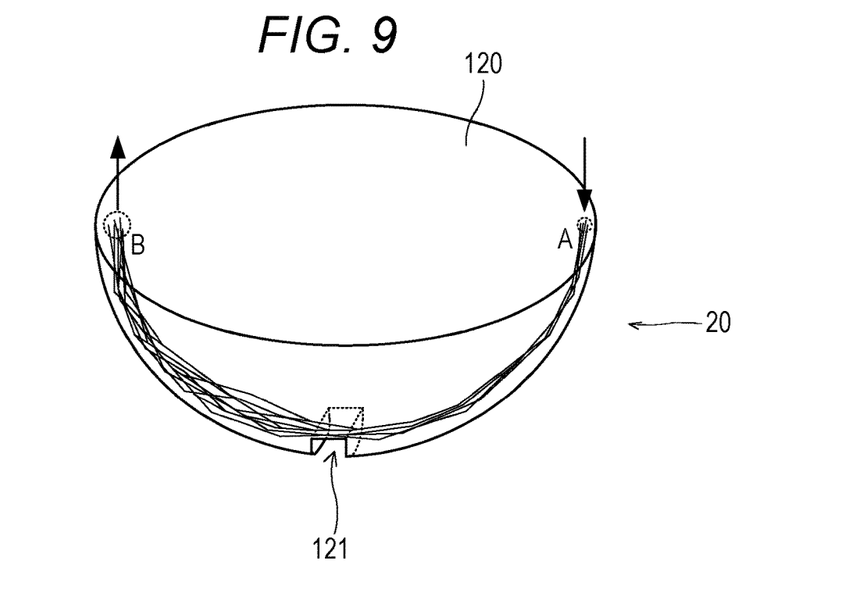
FIG. 9 illustrates the entrance of illumination light and the emission of measurement light in the transmission probe specific optical element.

When light is incident on an end A of a line segment of the main body 120 of such a transmission probe specific optical element 20, the line segment being formed by the plane of the hemisphere intersecting a plane (optical path plane) orthogonal to the walls of the gap 121, from a direction substantially perpendicular to the plane of the hemisphere as illustrated in FIG. 9, the light travels along an arc (an arc-shaped optical path) of the hemispherical surface near the optical path plane while repeating total reflection inside the hemisphere. The light further travels along the hemispherical surface across the gap 121, and goes out from an end B on the opposite side. In other words, the main body 120 of the transmission probe specific optical element 20 includes an arc-shaped optical path. The gap 121 is formed on the arc-shaped optical path in the main body 120.

Thus, as in the first example, by placing an emitting end of an irradiation purpose optical transmission path such that light is incident on the end A substantially perpendicularly to the plane of the hemisphere and placing an incident end of a measurement purpose optical transmission path at the end B, it is possible to allow irradiation light from the irradiation purpose optical transmission path to pass through the gap 121, and to guide the light (measurement light) that has passed through the gap 121 to the measurement purpose optical transmission path.

The light travels along the inner side of the hemisphere in the main body 120 of the transmission probe specific optical element 20. Hence, even if the gap 121 is formed extremely shallowly, the light can pass through the gap 121 portion. Hence, the entry of the sample solution can be facilitated with a simple configuration by applying the transmission probe specific optical element 20 to a head section of a transmission probe.

The material, usage, modification and the like of the main body 120 of the transmission probe specific optical element 20 according to the second example are similar to those of the transmission probe specific optical element 10 according to the first example. The main body 120 of the transmission probe specific optical element 20 may not be strictly hemispherical, and in particular, may have any shape especially at a location other than the optical path plane.

Figure 10:
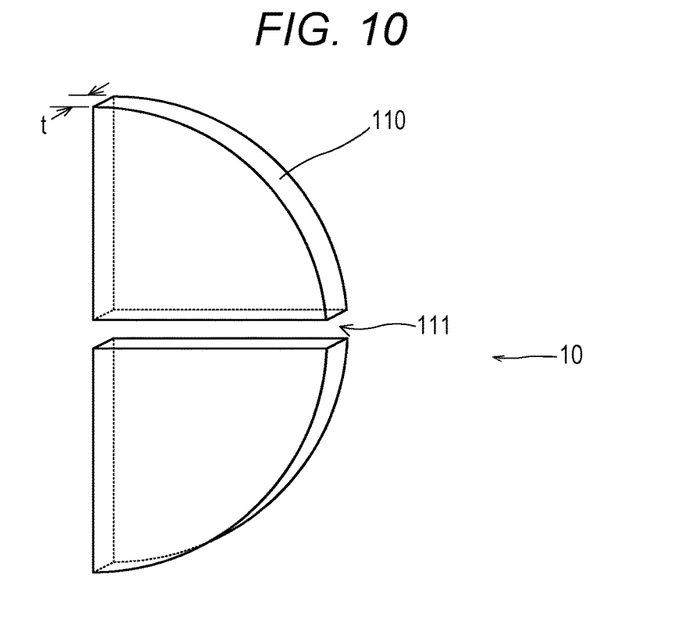
FIG. 10 illustrates a modification of the transmission probe specific optical element.

In the above-mentioned first example, the notch-shaped gap 111 is formed to have a predetermined depth. Instead of this, the gap 111 may penetrate through to an opposite surface (a straight portion) as illustrated in FIG. 10. In other words, the gap 111 may not be shaped into a notch, but may be shaped into a through groove. In this case, the main body 110 of the transmission probe specific optical element 10 is divided into two parts by the gap 111. Similarly, in the second example, the gap 121 may penetrate through to an opposite surface (the plane of the hemisphere). In other words, the gap 121 may not be shaped into a notch, but may be shaped into a hole or through groove. In this case, the main body 120 of the transmission probe specific optical element 20 may be divided into two parts by the gap 121.

It can also be said that the embodiment of the present disclosure relates to a technique for facilitating the entry of the sample solution into the gap when light is applied to the sample solution in the gap to take transmission measurements.

As illustrated in FIG. 6, the flange portion 115 may be formed in the side surface direction to facilitate the handling of the transmission probe specific optical element 10.

In the second example, it can also be said that when light is incident on the end A of the line segment of the main body 120 of the transmission probe specific optical element 20, the line segment being formed by the plane of the hemisphere intersecting the plane (the optical path plane) intersecting the walls of the gap 121 at the right angle, in the direction perpendicular to the plane of the hemisphere, as illustrated in FIG. 9, the light travels along the hemispherical surface near the optical path plane while repeating total reflection inside the hemisphere. The light further travels along the hemispherical surface across the gap 121, and goes out from the end B on the opposite side.

Embodiments of the present disclosure may include the following first to third optical elements used for immersion transmission measurements (optical elements), first transmission probe, first sample container, first optical device, and first immersion transmission measurement method.

The first optical element is a semicircular plate-shaped light transmissive material and includes a notch-shaped gap formed on part of the semi-circumference.

The second optical element is a hemispherical light transmissive material and includes a notch-shaped gap formed on part of the hemispherical surface.

In the third optical element according to the first or second optical element, an inclined surface or rounding is provided to one corner on the notched side of the gap.

The first transmission probe includes a distal end to which any of the first to third optical elements is attached, emits irradiation light to the optical element such that total reflection occurs on an inner surface of the optical element, and lets in return light from the optical element across the gap as measurement light.

The first sample container includes an inner surface to which any of the first to third optical elements is attached.

The first optical device is attached to the first sample container, emits the irradiation light to the optical element such that total reflection occurs on the inner surface of the optical element, and lets in the return light from the optical element across the gap as the measurement light.

The first immersion transmission measurement method includes the steps of attaching the first or the second optical element to the inner surface of the sample container, emitting the irradiation light to the optical element from outside the sample container such that total reflection occurs on the inner surface of the optical element, and letting in the return light from the optical element across the gap as the measurement light.

According to the first to third optical elements, the first transmission probe, the first sample container, the first optical device, and the first immersion transmission measurement method, it is possible to facilitate the entry of a sample solution into the gap when light is applied to the sample solution in the gap to take transmission measurements.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An optical element comprising:
   a main body formed of a light transmissive material and including an arc-shaped optical path inside the light transmissive material and on an inner circumferential surface of the main body; and
   a notch formed on the arc-shaped optical path in the main body, the notch extending from an end surface of the optical element to an inner portion of the main body,
   wherein the optical element is configured to receive light from a light source such that the light travels along the arc-shaped optical path and total reflection occurs on the inner circumferential surface of the main body.

2. The optical element according to claim 1, wherein the main body has a semicircular plate shape.

3. The optical element according to claim 2, further comprising a flange portion provided to a diameter portion of the main body having the semicircular plate shape.

4. The optical element according to claim 1, wherein the main body has a hemispherical shape.

5. The optical element according to claim 1, further comprising an inclined surface or curved surface formed at one corner on the notch.

6. The optical element according to claim 1, wherein the notch has a groove shape.

7. The optical device according to claim 2, wherein the notch has a V-shape, square shape, or circular shape.

8. A transmission probe comprising:
   the optical element according to claim 1;
   an irradiation purpose optical transmission path configured to emit irradiation light to the optical element such that total reflection occurs on the inner circumferential surface of the main body; and
   a measurement purpose optical transmission path configured to receive, as measurement light, return light passing through the gap of the optical element to be emitted from the optical path.

9. A sample container comprising:
   the optical element according to claim 1; and
   wherein a proximal end of the optical element is attached to an inner surface of the sample container.

10. An optical device comprising:
    the sample container according to claim 9;
    an irradiation purpose optical transmission path configured to emit irradiation light to the optical element such that total reflection occurs on the inner circumferential surface of the main body; and
    a measurement purpose optical transmission path configured to receive, as measurement light, return light passing through the notch of the optical element to be emitted from the optical path,
    wherein the optical device resides outside the sample container.

11. The optical device according to claim 10, wherein the optical device includes at least one guide member configured to align the irradiation purpose optical transmission path and the measurement purpose optical transmission path with the optical element.

12. The optical device according to claim 10, wherein the sample container includes at least one guide member configured to align the irradiation purpose optical transmission path and the measurement purpose optical transmission path with the optical element.

13. The sample container according to claim 9, wherein the proximal end of the optical element is attached to either a side surface or a bottom surface of the sample container.

14. An immersion transmission measurement method comprising:
    attaching the optical element according to claim 1 to an inner surface of a sample container;
    emitting irradiation light from outside the sample container to the optical element such that total reflection occurs on an inner surface of the optical path of the optical element; and
    receiving, as measurement light, return light passing through the notch of the optical element to be emitted from the optical path.

15. An optical transmission system comprising:
    an optical element including a main body and an arc-shaped optical path inside a light transmissive material and on an inner circumferential surface of the main body, and a notch formed on the arc-shaped optical path in the main body, the notch extending from an end surface of the optical element to an inner portion of the main body;
    an optical device including:
      an irradiation purpose optical transmission path configured to emit irradiation light to the optical element such that total reflection occurs on the inner circumferential surface of the main body, and
      a measurement purpose optical transmission path configured to receive, as measurement light, return light passing through the notch of the optical element to be emitted from the arc-shaped optical path; and
    a sample container,
    wherein a proximal end of the main body is attached to an inner surface of the sample container, and
    wherein the whole of the optical device resides outside the sample container.

16. The optical transmission system of claim 15, wherein a portion of a wall of the sample container separates the main body from the optical device.

* * * * *